US011469000B2

(12) United States Patent
Kido

(10) Patent No.: US 11,469,000 B2
(45) Date of Patent: Oct. 11, 2022

(54) MEDICAL INFORMATION PROCESSING DEVICE, MEDICAL INFORMATION PROCESSING METHOD, AND STORAGE MEDIUM

(71) Applicant: Hitachi, Ltd., Tokyo (JP)

(72) Inventor: Kunihiko Kido, Tokyo (JP)

(73) Assignee: HITACHI, LTD., Tokyo (JP)

( * ) Notice: Subject to any disclaimer, the term of this patent is extended or adjusted under 35 U.S.C. 154(b) by 49 days.

(21) Appl. No.: 17/054,795

(22) PCT Filed: Feb. 20, 2019

(86) PCT No.: PCT/JP2019/006416
§ 371 (c)(1),
(2) Date: Nov. 12, 2020

(87) PCT Pub. No.: WO2019/230073
PCT Pub. Date: Dec. 5, 2019

(65) Prior Publication Data
US 2021/0233666 A1  Jul. 29, 2021

(30) Foreign Application Priority Data
May 29, 2018 (JP) .............................. JP2018-102099

(51) Int. Cl.
*G16H 70/40* (2018.01)
*G16H 10/00* (2018.01)

(52) U.S. Cl.
CPC ............ *G16H 70/40* (2018.01); *G16H 10/00* (2018.01)

(58) Field of Classification Search
CPC ................................ G16H 70/40; G16H 10/00
(Continued)

(56) References Cited

U.S. PATENT DOCUMENTS 9,649,469 B2 * 5/2017 Hyde ..................... G16H 20/10
11,151,982 B2 * 10/2021 Tomkins ................ G06N 20/00
(Continued)

FOREIGN PATENT DOCUMENTS

| JP | 2008-210414 A | 9/2008 |
| JP | 2017-174406 A | 9/2017 |
| JP | 2017174405 A | 9/2017 |

OTHER PUBLICATIONS

Bates et al.: Big Data in Health Care: Using Analytics to Identify and Manage High-Risk and High-Cost Patients; Jul. 2014; Health Affairs, 33:7; pp. 1123-1131; doi: 10.1377/hlthaff.2014.0041 (Year: 2014).*

(Continued)

*Primary Examiner* — Joy Chng
(74) *Attorney, Agent, or Firm* — Mattingly & Malur, PC

(57) ABSTRACT

A device that holds a medical dictionary indicating medical concepts, drug information, medical care information and documents indicating a medical concept not included in the medical care information, identifies from the documents, for each combination of a medical concept not included in the medical care information and a drug included in the drug information, a document indicating the medical concept and the drug. The device generates a medical concept list including the medical concept indicated by the medical dictionary included in each identified document and determines, based on a probability of each medical concept not included in the medical care information appearing in a context of the document indicated by the medical concept list, from among the medical concepts not included in the medical care information, a medical concept having an influence on a prescription of the drug included in the drug information.

7 Claims, 9 Drawing Sheets

(58) Field of Classification Search
USPC .......................................................... 705/2–3
See application file for complete search history.

(56) References Cited

U.S. PATENT DOCUMENTS

| 2004/0249669 A1 | 12/2004 | Pollack et al. |
| 2017/0277856 A1 | 9/2017 | De La Torre et al. |
| 2017/0277857 A1 | 9/2017 | De La Torre et al. |

OTHER PUBLICATIONS

Awaysheh et al.: "A review of medical terminology standards and structured reporting." Journal of veterinary diagnostic investigation: official publication of the American Association of Veterinary Laboratory Diagnosticians, Inc vol. 30,1 (2018): 17-25. doi:10.1177/1040638717738276 (Year: 2018).*

International Search Report of PCT/JP2019/006416 dated May 28, 2019.

* cited by examiner

| REAL WORLD DATA 210 | | | | | | | |
|---|---|---|---|---|---|---|---|
| PATIENT ID | ENCOUNTER ID | DISEASE NAME | PRE-SCRIPTION | TEST RESULT | TREAT-MENT | INPATIENT/ OUTPATIENT | DATE |
| 100 | 100 | DIABETES | DRUG A | HbA1c: 10% | - | OUTPATIENT | 2018/1/10 |
| 100 | 200 | DIABETES | DRUG A | HbA1c: 9% | - | OUTPATIENT | 2018/2/10 |
| ... | ... | ... | ... | ... | ... | ... | ... |

211  212  213  214  215  216  217  218

MEDICAL INFORMATION PROCESSING DEVICE, MEDICAL INFORMATION PROCESSING METHOD, AND STORAGE MEDIUM

CLAIM OF PRIORITY

The present application claims priority from Japanese patent application JP 2018-102099 filed on May 29, 2018, the content of which is hereby incorporated by reference into this application.

BACKGROUND

The present invention relates to a medical information processing device, a medical information processing method, and a storage medium.

As a background art of the technical field of the present invention, there is JP 2008-210414 A. In JP 2008-210414 A, it is described that "A computer device of this invention is configured to: link to a history database of vertical prescription data acquired form a retail pharmacy; determine whether or not it is possible to track on the database a patient who is to remain confidential in association with a specific prescription; compare, when it is possible to track the patient, a medication amount and a prescription product in the specified prescription with a medication amount and a prescription product of another prescription for the patient who is to remain confidential in the database; classify the specific prescription based on a change in the medication amount or the prescribed medication between the specific prescription and the another prescription as one of a plurality of different prescription classifications based on a corresponding number of classification variables; count a total number of the prescriptions; generate a prediction model related to the classification variables based on the total number of prescriptions in response to generation of a market event; and display the prediction of the prescription practice of the doctor to issue a warning" (refer to Abstract).

The technology described in JP 2008-210414 A predicts a prescription practice by a doctor by analyzing past prescription data. However, not only information included in medical care information, for example, prescription data, but also information not appearing in medical care information, such as quality of life (QoL) and activities of daily living (ADL), have an influence on determination of a prescribed drug, but the technology described in JP 2008-210414 A does not evaluate the influence of such information.

SUMMARY OF THE INVENTION

Therefore, according to one mode of the present invention is aimed to evaluate the influence of information not obtainable from medical care information, such as a QoL index and an ADL index, on the determination of a prescribed drug.

In order to solve the above problem, one mode of the present invention applies the following constitutions. a medical information processing device, comprising: a processor; and a memory, the memory being configured to hold: a medical dictionary indicating a list of medical concepts; drug information indicating a name of a drug; medical care information including a medical care history; and documents each including a description about a medical concept other than a medical concept included in the medical care information, the processor being configured to: identify from the documents, for each combination of a medical concept other than the medical concept included in the medical care information and a drug included in the drug information, a document including the description about the medical concept and the description about the drug; generate, for each combination, a medical concept list including the medical concept indicated by the medical dictionary included in each identified document; and determine, based on a probability of each medical concept other than the medical concept included in the medical care information appearing in a context of the document indicated by the medical concept list, from among the medical concepts other than the medical concept included in the medical care information, a first medical concept having an influence on a prescription of the drug included in the drug information.

One mode of the present invention can evaluate the influence of information not obtainable from medical care information, such as a QoL index and an ADL index, on the determination of a prescribed drug.

Problems, configurations, and effects which are not mentioned above are explained in the following embodiments.

BRIEF DESCRIPTIONS OF DRAWINGS

The present invention can be appreciated by the description which follows in conjunction with the following figures, wherein.

FIRST EMBODIMENT

Figure 1:
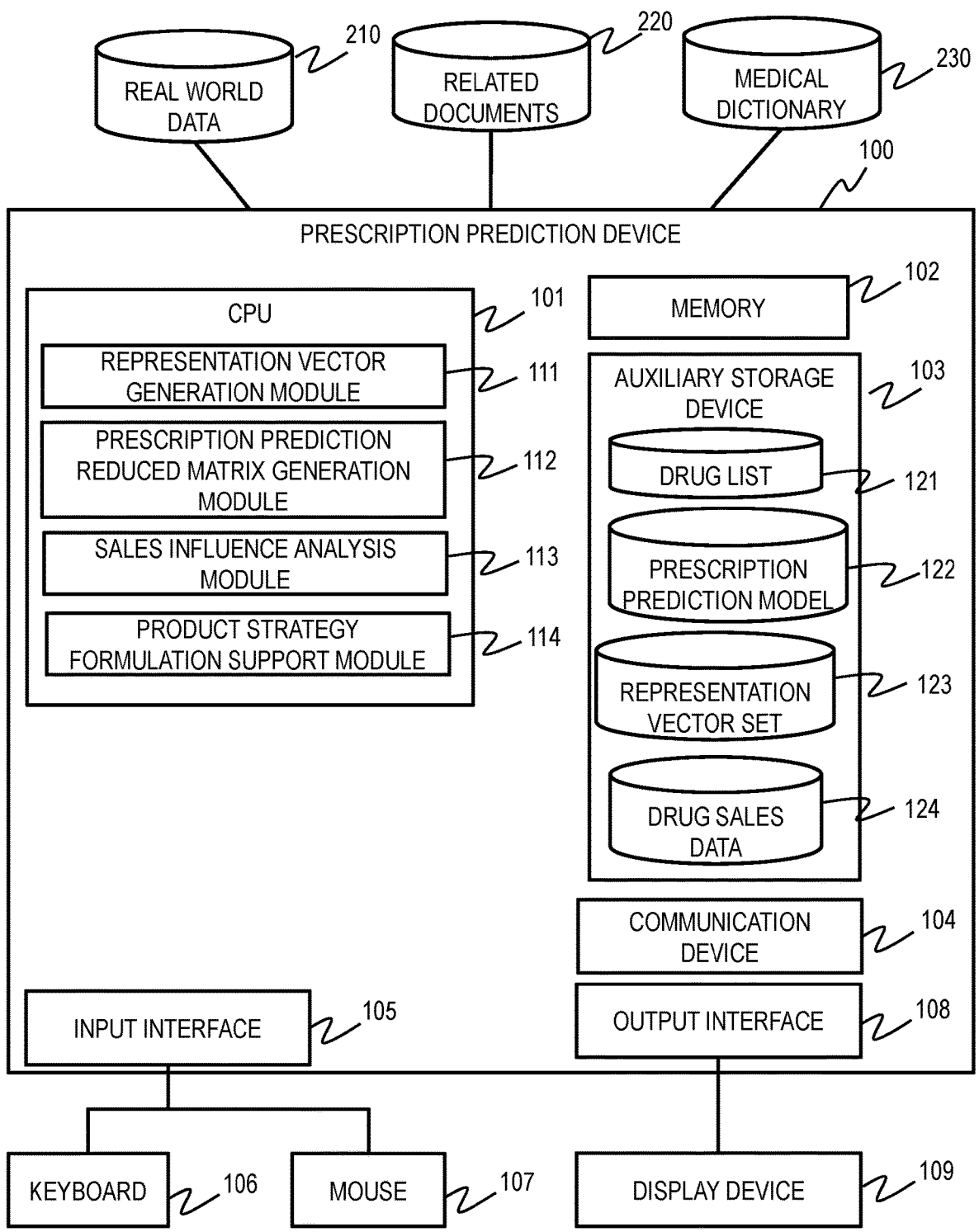
FIG. 1 is a block diagram for illustrating a configuration example of the prescription prediction device.

In the following, an embodiment of the present invention is explained referring the attached drawings. The embodiment is an example to achieve the present invention and does not limit a technical range of the present invention. In the drawings, the same configuration has the same reference letter.

In a first embodiment of the present invention, there is described a prescription prediction device, which is an example of a medical information processing device. FIG. 1 is a block diagram for illustrating a configuration example of the prescription prediction device. A prescription prediction device 100 is constructed from a computer including a central processing unit (CPU) 101, a memory 102, an auxiliary storage device 103, and a communication device 104.

The CPU 101 includes a processor, and is configured to execute a program stored in the memory 102. The memory 102 includes a read only memory (ROM), which is a nonvolatile memory device, and a random access memory (RAM), which is a volatile memory device. The ROM stores, for example, an invariant program (for example, basic input/output system (BIOS)). The RAM is a dynamic random access memory (DRAM) or other such high-speed volatile memory device, and temporarily stores a program to be executed by the CPU 101 and data to be used at a time of execution of the program.

The auxiliary storage device 103 is, for example, a large-capacity and non-volatile storage device such as a magnetic storage device (hard disk drive (HDD)) and a flash memory (solid state drive (SSD)). Programs and data to be used when the programs are executed by the CPU 101 are stored in the auxiliary storage device 103. Specifically, the programs are read from the auxiliary storage device 103, loaded onto the memory 102, and executed by the CPU 101.

The prescription prediction device 100 may include an input interface 105 and an output interface 108. The input interface 105 is an interface coupled to a keyboard 106, a mouse 107, and the like, and is configured to receive input from an operator. The output interface 108 is an interface coupled to a display device 109, a printer, and the like, and is configured to output an execution result of a program in a format that is visually recognizable by the operator.

The communication device 104 is a network interface device configured to control communication to and from another device in accordance with a predetermined protocol. The communication device 104 includes, for example, a serial interface such as USB.

The programs to be executed by the CPU 101 are provided to the prescription prediction device 100 through intermediation of a removable medium (for example, CD-ROM or flash memory) or through the network, and is stored in the nonvolatile auxiliary memory device 103 being a non-transitory storage medium. Therefore, the prescription prediction device 100 preferably includes an interface configured to read data from the removable medium.

The prescription prediction device 100 is a computer system formed on physically one computer or formed on a plurality of computers that are configured logically or physically, and may be operated on separate threads on the same computer, or may operate on a virtual machine built on a plurality of physical computer resources.

The CPU 101 includes a representation vector generation module 111, a prescription prediction reduced matrix generation module 112, a sales influence analysis module 113, and a product strategy formulation support module 114. For example, the CPU 101 functions as the representation vector generation module 111 by operating in accordance with a representation vector generation program loaded onto the memory 102, and functions as the prescription prediction reduced matrix generation module 112 by operating in accordance with a prescription prediction reduced matrix generation program loaded onto the memory 102. The relationship between the programs and the other functional modules included in the CPU 101 is also the same.

A part or all of the functions of the functional modules included in the CPU 101 may be implemented by hardware such as an application specific integrated circuit (ASIC) and a field-programmable gate array (FPGA).

The representation vector generation module 111 is configured to generate a representation vector. The prescription prediction reduced matrix generation module 112 is configured to generate a prescription prediction reduced matrix.

The sales influence analysis module 113 is configured to analyze the degree to which each index indicating the characteristics of a certain drug contributes to the prescription of the drug. The product strategy formulation support module 114 is configured to retrieve a drug similar to a target drug (for example, a newly developed drug) not included in the drugs indicated by a representation vector set 123 described later and information on the similar drug.

The auxiliary storage device 103 holds a drug list 121, a prescription prediction model 122, a representation vector set 123, and drug sales data 124. The drug list 121 is an example of drug information including a list of drug names. A part or all of the data stored in the auxiliary storage device 103 may be stored in a database coupled to the prescription prediction device 100.

The prescription prediction model 122 is a model for outputting a vector indicating a predicted drug when an encounter vector described later is input. The prescription prediction model 122 is defined by, for example, a neural network. The prescription prediction reduced matrix described later is an example of a parameter of the prescription prediction model 122. In a calculation of a predicted drug using the prescription prediction model 122, the product of the encounter vector and the prescription prediction matrix described later is calculated.

The representation vector set 123 includes representation vectors described later. The drug sales data 124 includes, for example, time series information on sales of each drug.

The prescription prediction device 100 is coupled to a database holding real world data 210, related documents 220, and a medical dictionary 230. The real world data 210, the related documents 220, and the medical dictionary 230 may be stored in the auxiliary storage device 103.

The real world data 210 is an example of medical care information holding information on actual medical care, including receipt data, medical chart data, medical checkup data, and the like. Medical care includes actions such as a medical examination, a medical treatment, a prescription, a medical checkup, and a test performed by a doctor on a patient. In the first embodiment, the real world data 210 does not hold information indicating the QoL and the ADL. At least document included in the related documents 220 includes information indicating the QoL and the ADL not included in the real world data 210.

The medical dictionary 230 holds medical concepts, a network representing a relationship among the medical concepts, and information indicating whether or not the medical concepts are concepts relating to a numerical value. Examples of medical concepts include a disease name, a drug name, a test name, a test result, an index name indicating the QoL, an index name indicating the ADL, an event name related to a medical treatment (for example, an adverse event), and a medical term. Concepts relating to a numerical value are concepts that can indicate a specific phenomenon by a numerical value.

In the first embodiment, the information used by the prescription prediction device 100 is not dependent on the data structure, and may be represented by any data structure. For example, a data structure suitably selected from a table, a list, a database, or a queue can store the information.

Figures 2A, 2B:
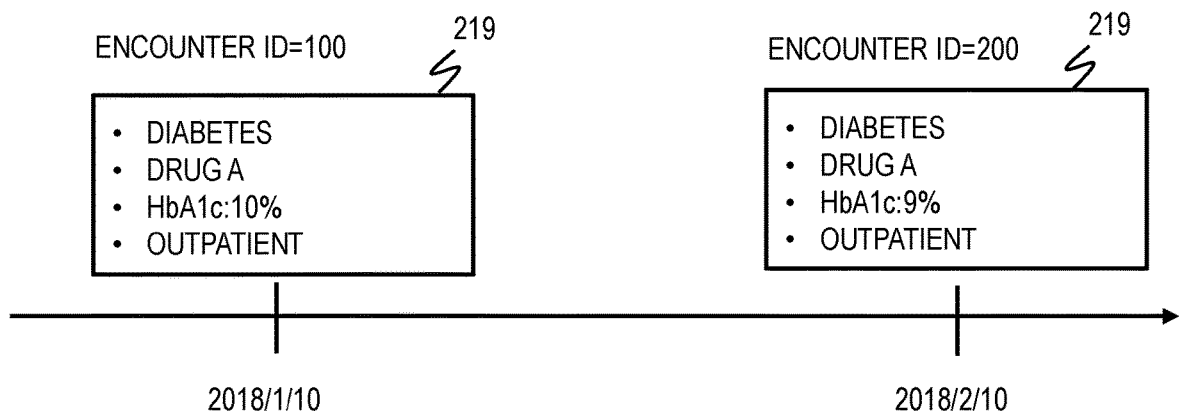
FIG. 2A is a table for showing an example of the real world data.
FIG. 2B is an explanatory diagram for illustrating an example of medical care identified by the real world data.

FIG. 2A is a table for showing an example of the real world data 210. The real world data 210 includes, for example, a patient ID column 211, an encounter ID column 212, a disease name column 213, a prescription column 214, a test result column 215, a treatment column 216, an inpatient/outpatient column 217, and a date column 218.

The patient ID column 211 stores an ID for identifying a patient. The encounter ID column 212 stores an ID for identifying the medical care to be given. The disease name column 213 stores the name of the disease for which the medical care is to be given. The prescription column 214 stores the name of the drug prescribed for the medical care. The test result column 215 stores the result of the test performed in the medical care. The treatment column 216 stores the name of the treatment performed in the medical care.

The inpatient/outpatient column 217 stores information indicating whether the medical care is for an inpatient or an outpatient. The date column 218 stores the date on which the medical care is performed. In the example of FIG. 2A, a null value stored in the treatment column 216 indicates that, for example, treatment is not performed or it is unknown whether treatment is performed in the medical care. The same applies to cases in which a null value is stored in other columns.

FIG. 2B is an explanatory diagram for illustrating an example of medical care identified by the real world data 210 of FIG. 2A. In FIG. 2B, there is illustrated medical care performed on a patient A. The patient A received medical care having an encounter ID of 100 on Jan. 10, 2018. The disease name, which is the name of the disease for which the medical care is to be given, is diabetes, drug A is prescribed, the test result is "HbA1c is 10%", and the medical care is received by an outpatient.

The patient A also received the medical care having an encounter ID of "200" on Feb. 10, 2018. The disease name, which is the name of the disease for which the medical care is to be given, is diabetes, drug A is prescribed, the test result is "HbA1c is 9%", and the medical care is received by an outpatient.

Among the values included in the records of the real world data 210, the values related to the content of the medical care is also referred to as "encounter information 219". In the example of FIG. 2B, the encounter information 219 is information including, of the values included in the records of the real world data 210, the information on the values other than for the patient ID, the encounter ID, the date, and null values. In the example of FIG. 2B, the encounter information 219 for the encounter ID=100 includes "diabetes", "drug A", "HbA1c: 10%", and "outpatient".

Figure 3:
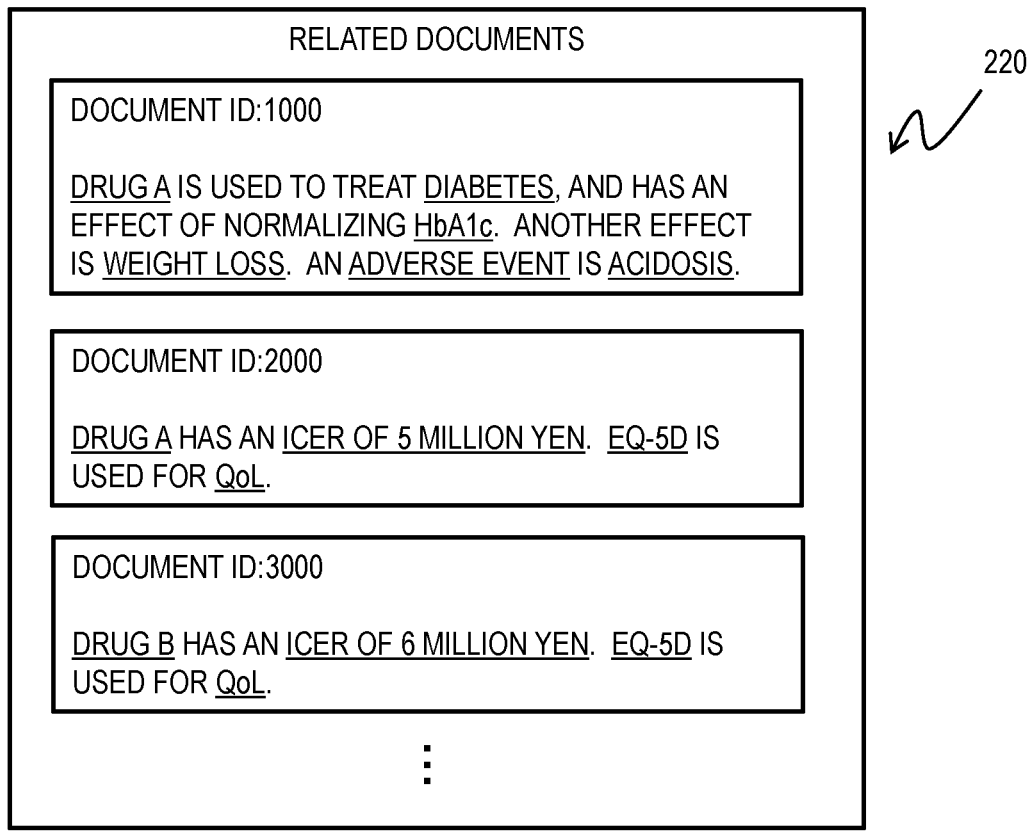
FIG. 3 shows an example of the related documents.

FIG. 3 shows an example of the related documents 220. The related documents 220 include one or more documents, and each document is given a document ID for identifying the document. It should be noted that an incremental cost effectiveness ratio (ICER) in the document having the document ID of "2000" and the document having the document ID of "3000" is an example of an index relating to the QoL.

The underlined words in the documents of FIG. 3 are medical concepts included in the medical dictionary 230 or drug names included in the drug list 121 (as described above, drug names are also an example of a medical concept). As illustrated in FIG. 3, each document may hold a medical concept in the document in a form capable of discriminating the medical concept, and the function modules referring to the document in the processing described later may identify the medical concept in the document by referring to the medical dictionary 230.

Figure 4:
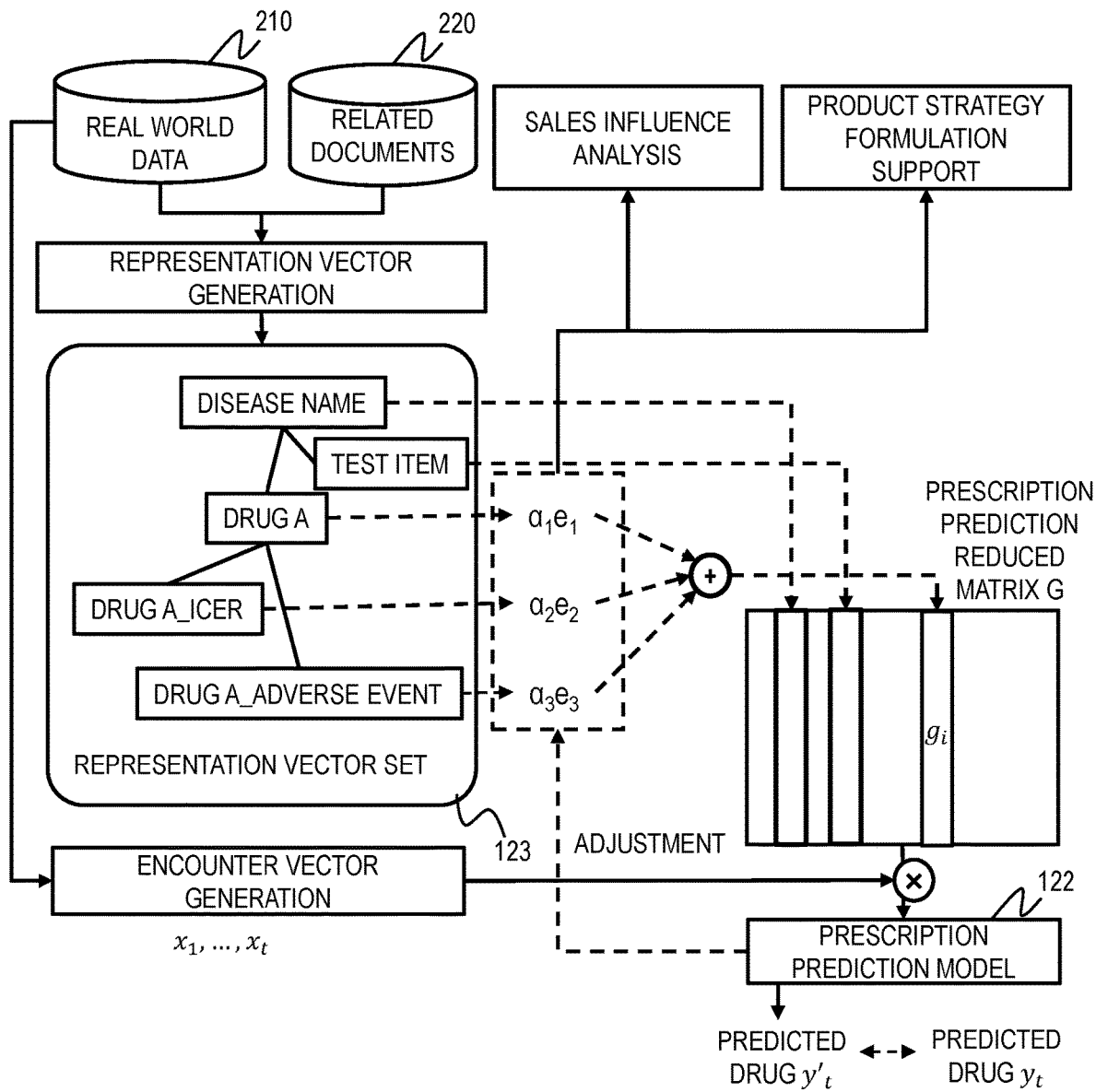
FIG. 4 is an explanatory diagram for illustrating an example of an outline of overall processing by the prescription prediction device.

FIG. 4 is an explanatory diagram for illustrating an example of an outline of overall processing by the prescription prediction device 100. The representation vector generation module 111 generates representation vectors based on the real world data 210 and the related documents 220. The representation vectors are obtained from, for example, a medical concept appearing in the related documents 220 in co-occurrence with the target drug, or a medical concept appearing in the real world data 210. The representation vectors have an influence on the determination of the prescribed drug in the prescription prediction model 122. When the phenotypic vectors are obtained from a medical concept co-occurring with the target drug in the related documents 220, the medical concept has an influence on (contributes to) the prescription of the target drug in the prescription prediction model 122.

The prescription prediction reduced matrix generation module 112 calculates, for each drug, a linear sum obtained by weighting the representation vectors in a network centered on the drug. The weight indicates the degree of influence (degree of contribution) that the medical concept indicated by the corresponding representation vector has on the prescription of the drug indicated by the representation vector. The prescription prediction reduced matrix generation module 112 arranges each calculated linear sum and other representation vectors to generate a prescription prediction reduced matrix G.

The prescription prediction reduced matrix generation module 112 generates an encounter vector from the encounter information 219. The prescription prediction reduced matrix generation module 112 compares the predicted drug obtained by inputting the encounter vector into the prescription prediction model 122 with the prescribed drug in the encounter information, and updates the parameters in the prescription prediction model 122.

The sales influence analysis module 113 evaluates, for a given drug, the factors influencing the prescription of the drug based on the weights corresponding to the representation vectors in a network centered on the drug. The product strategy formulation support module 114 estimates, based on the representation vectors in the network centered on the drugs included in the representation vector set 123 and the weights corresponding to the representation vectors, a drug similar to a target drug (for example, a newly developed drug) not included in the representation vector set 123.

Figure 5:
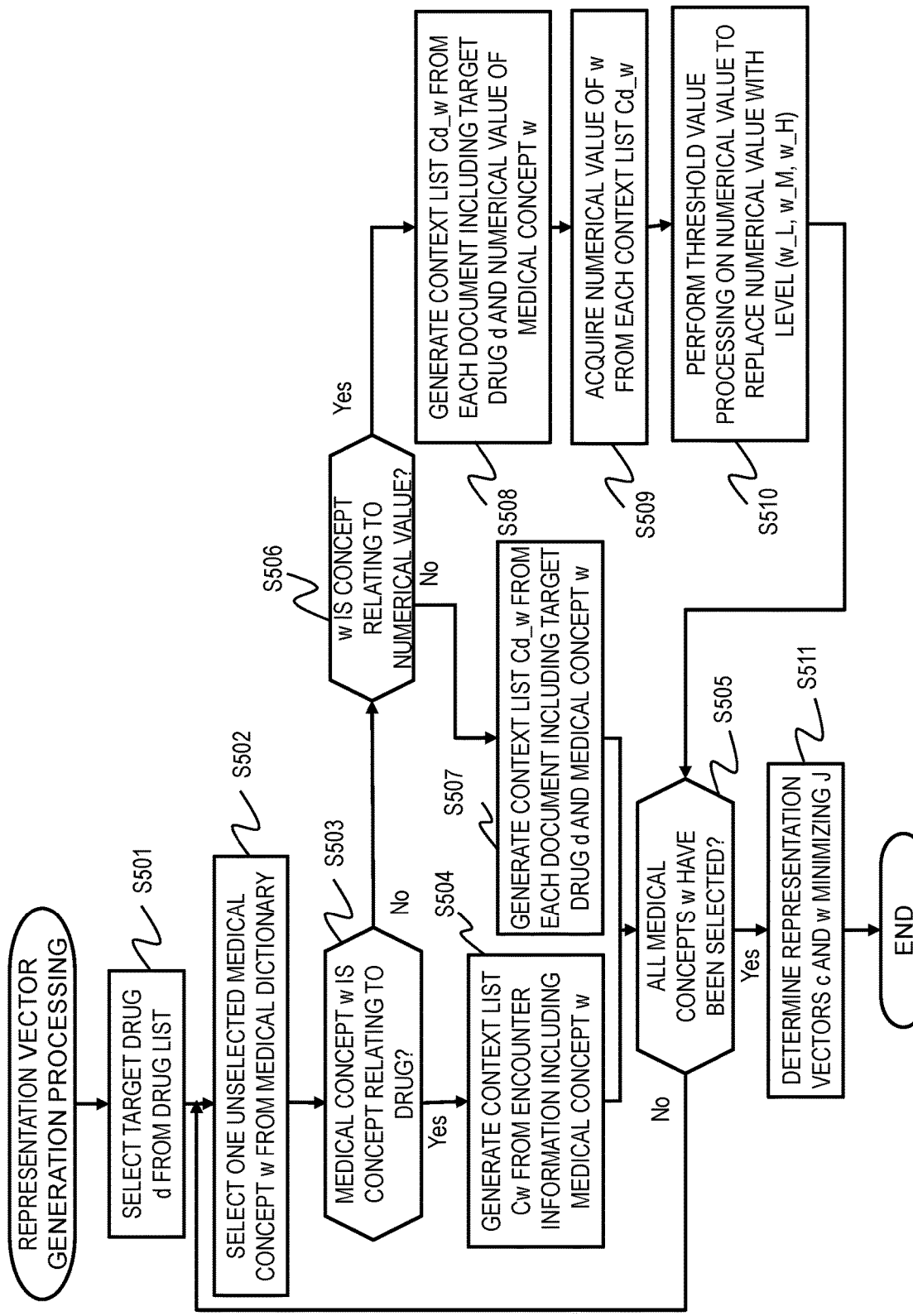
FIG. 5 is a flowchart for illustrating an example of representation vector generation processing.

FIG. 5 is a flowchart for illustrating an example of representation vector generation processing. The representation vector generation module 111 selects one or more target drugs d from the drug list 121 (Step S501). The target drugs to be selected may be, for example, all the drugs included in the drug list 121, or may be drugs designated by the user via the input interface 105 or from another device via the communication device 104.

The representation vector generation module 111 selects one unselected medical concept w from among the selection target medical concepts included in the medical dictionary 230 (Step S502). The selection target medical concepts may be, for example, all the medical concepts included in the medical dictionary 230, or may be medical concepts designated by the user via the input interface 105 or from another device via the communication device 104. It is not required that the selection target medical concepts include the medical concepts included in the real world data 210.

The representation vector generation module 111 determines whether the medical concept w is included in the real world data 210 (Step S503). When it is determined that the medical concept w is included in the real world data 210 (Step S503: Yes), the representation vector generation module 111 refers to the real world data 210, and generates one or more context lists Cw (Step S504).

In Step S504, for example, the representation vector generation module 111 acquires the encounter information on each record including the medical concept w from the real world data 210. The representation vector generation module 111 generates, for each piece of encounter information, a list having, as an element, a value other than the medical concept w among the values included in the encounter information, and determines the generated list as the context list Cw. Specifically, the context list Cw indicates a group of words co-occurring in the medical concept w.

For example, when the medical concept w is "diabetes", in Step S504, from the real world data 210 of FIG. 2A, a context list $C_{diabetes\_1}$={drug A, test result HbA1c: 10%, outpatient} and a context list $C_{diabetes\_2}$={drug A, test result HbA1c: 9%, outpatient} are generated.

Then, the representation vector generation module 111 determines whether or not all of the selection target medical concepts have been selected (Step S505). When it is determined that, among the selection target medical concepts, there is a medical concept yet to be selected (Step S505: Yes), the representation vector generation module 111 returns to Step S502. The processing performed when the representation vector generation module 111 determines that all of the selection target medical concepts have been selected (Step S505: Yes) is described later.

When it is determined that the medical concept w is not included in the real world data 210 (Step S503: No), the representation vector generation module 111 refers to the medical dictionary 230, and determines whether or not the medical concept w is a concept relating to a numerical value (Step S506). When it is determined that the medical concept w is not a concept relating to a numerical value (Step S506: No), the representation vector generation module 111 refers to the related documents 220, generates a context list Cd_w for each target drug d (Step S507), and advances to Step S505.

In Step S507, the representation vector generation module 111 identifies the document including, for example, the medical concept w and at least one target drug from the related documents 220. The representation vector generation module 111 generates, for each combination of each target drug d and each identified document, a list having, as elements, the medical concept w included in the document and each medical concept other than the target drug d, and determines the generated list to be the context list Cd_w. Specifically, the context list Cd_w indicates a group of words co-occurring in the drug d and the medical concept w.

For example, when the medical concept w is an "adverse event" and the target drug d is "drug A", in Step S507, $C_{drug\_A\_adverse\_event}$={acidosis, diabetes, HbA1c, weight loss} is generated as the context list from the document having the document ID of "1000" in the example of FIG. 3.

It should be noted that, in Step S507, when the representation vector generation module 111 generates the context list Cd_w from the identified document, for example, the representation vector generation module 111 may obtain the medical concept to be included in the context list Cd_w from the entire document or may obtain the medical concept to be included in the context list Cd_w from a predetermined range of sentences including, from among the sentences included in the document, a sentence including the medical concept w and a sentence including the drug d. Further, when the value of a distance between the medical concept w and the target drug d is large in the identified document (for example, when there are a predetermined number or more words or characters between the medical concept w and the target drug d), for example, the representation vector generation module 111 may exclude the document from the Cd_w generation targets.

When it is determined that the medical concept w is a concept relating to a numerical value (Step S506: Yes), the representation vector generation module 111 refers to the related documents 220, and generates a context list Cd_w for each target drug d (Step S508).

In Step S508, the representation vector generation module 111 identifies the document including, for example, a numerical value of the medical concept w and at least one target drug d from the related documents 220. The representation vector generation module 111 generates, for each combination of each target drug d and each identified document, a list having, as elements, each medical concept other than the target drug d included in the document and the numerical value of the medical concept w, and determines the generated list to be the context list Cd_w. Specifically, the context list Cd_w indicates a group of words co-occurring in the drug d and the medical concept w.

For example, when the medical concept w is "ICER" and the target drug is "drug A", in Step S508, $C_{drug\_A\_ICER}$={diabetes, ICER=5 million yen, EQ-5D} is generated as the context list from the document having the document ID of "2000" in the example of FIG. 3. Similarly, when the medical concept w is "ICER" and the target drug is "drug B", in Step S508, $C_{drug\_B\_ICER}$={diabetes, ICER=6 million yen, EQ-5D} is generated as the context list from the document having the document ID of "2000" in the example of FIG. 3.

The representation vector generation module 111 acquires information indicating the numerical value of the medical concept w of each context list Cd_w generated in Step S508 (Step S509). In Step S509, the representation vector generation module 111 acquires, for example, "5 million" from $C_{drug\_A\_ICER}$={diabetes, ICER=5 million yen, EQ-5D}, and "6 million" from $C_{drug\_B\_ICER}$={diabetes, ICER=6 million yen, EQ-5D}.

The representation vector generation module 111 performs threshold value processing on the numerical values acquired in Step S509 to replace the information indicating the numerical value of w of the medical concept with the level obtained by the threshold value processing (Step S510), and advances to Step S505. For example, two threshold values in the threshold value processing are determined in advance for each medical concept relating to a numerical value.

In Step S510, the representation vector generation module 111, for example, determines that the level of the acquired numerical value is w_L when the numerical value is less than the smaller threshold value out of the two threshold values, determines that the level of the acquired numerical value is w_M when the numerical value is equal to or more than the smaller threshold value and the numerical value is less than the larger threshold value out of the two threshold values, and determines that the level of the acquired numerical value is w_H when the numerical value is equal to or more than the larger threshold value.

For example, when it is assumed that two threshold values, namely, 3 million and 5.5 million, are determined for ICER, which is a medical concept relating to a numerical value, in Step S510, the representation vector generation module 111 converts $C_{drug\_A\_ICER}$={diabetes, ICER=5 million yen, EQ-5D} into $C_{drug\_A\_ICER}$={diabetes, ICER_M, EQ-5D} and $C_{drug\_B\_ICER}$={diabetes, ICER_H, EQ-5D}.

The number of the threshold values in the threshold value processing may be one, three or more, or may differ for each concept relating to a numerical value.

When it is determined in Step S505 that all the selection target medical concepts have been selected (Step S505: Yes), the representation vector generation module 111 determines the c and w minimizing J shown in Expression 1 below to be the representation vectors, stores the determined representation vectors in the representation vector set 123 (Step S511), and ends the representation vector generation processing.

$$J = -\Sigma_{w \in \theta} \Sigma_{c \in C_w} \log(P(c|w)) \quad \text{(Expression 1)}$$

In Expression 1, θ is a set of words (medical concept) included in the medical dictionary 230, and Cw is a set of context lists including the word w among the context lists generated in Step S504, Step S507, and Step S508. Further, P(c|w) indicates the probability that the medical concept w appears in the context (in the document or the encounter information) indicated by the context list c, and is defined by the following Expression 2. Expression 2 is an expression used to determine a word vector and a context vector by a method, for example, word2vec, for the word w and the context list c.

$$P(c|w) = \frac{\exp(e_w \cdot e_c^T)}{\sum_{c' \in V} \exp(e_w \cdot e_{c'}^T)} \quad \text{(Expression 2)}$$

In Expression 2, V is a set of all the context lists generated in Step S504, Step S507, and Step S508, $\theta_w$ is a word vector of w, $\theta_c$ is a context vector of c, and $\theta_{c'}$ is a context vector of c'.

The representation vector represented by $\theta_w$ indicates that the medical concept w has an influence on the determination of the prescribed drug in the prescription prediction model 122.

Figure 6:
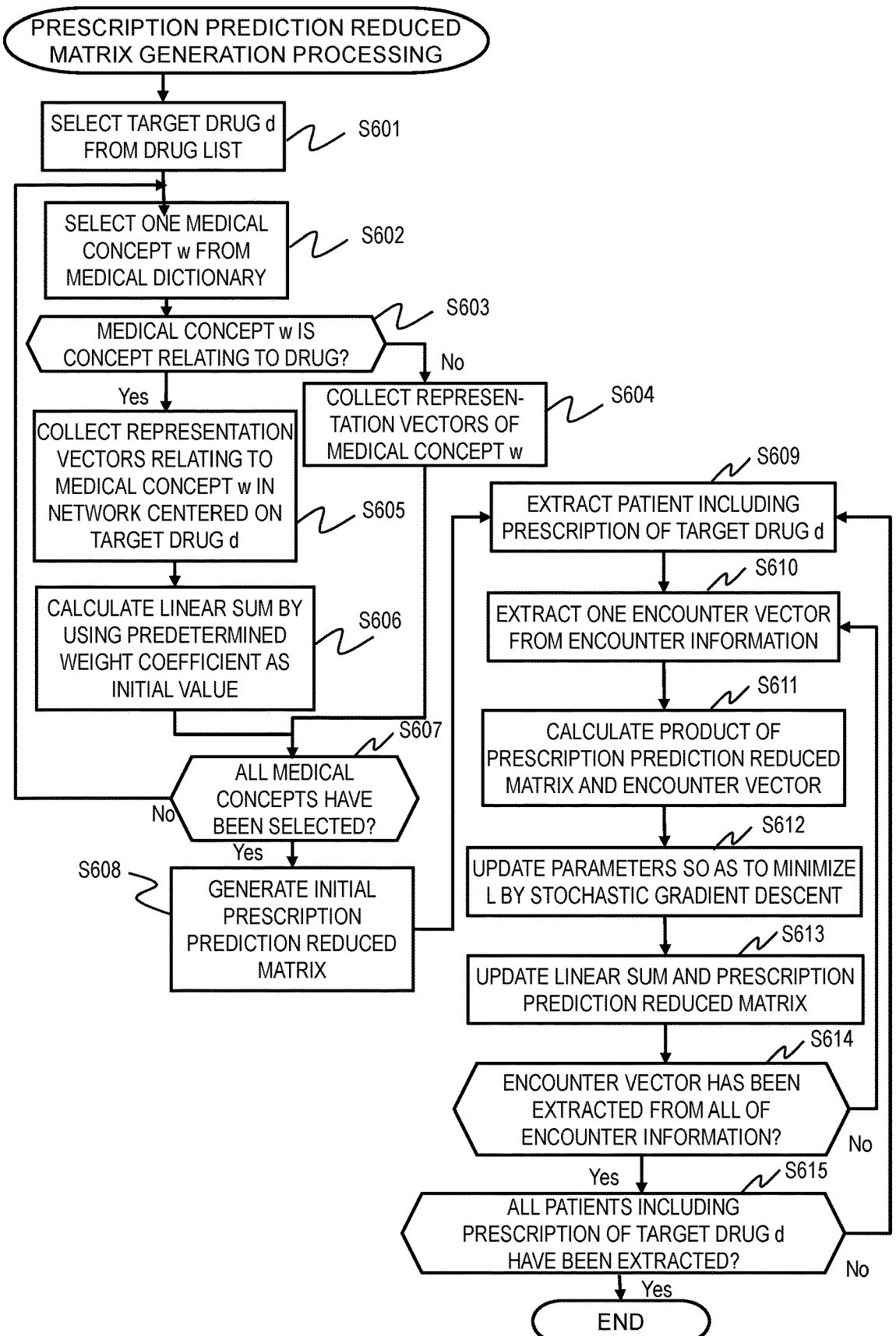
FIG. 6 is a flowchart for illustrating an example of the prescription prediction reduced matrix generation processing.

FIG. 6 is a flowchart for illustrating an example of the prescription prediction reduced matrix generation processing. The prescription prediction reduced matrix generation module 112 selects one or more target drugs d from the drug list 121 (Step S601). The target drugs to be selected may be, for example, all the drugs included in the drug list 121, or may be drugs that have been designated by the user via the input interface 105 or from another device via the communication device 104.

The prescription prediction reduced matrix generation module 112 selects one unselected medical concept w from among the selection target medical concepts included in the medical dictionary 230 (Step S602). The selection target medical concepts may be, for example, all the drugs included in the medical dictionary 230, or may be medical concepts designated by the user via the input interface 105 or from another device via the communication device 104.

The prescription prediction reduced matrix generation module 112 determines whether or not the selected medical concept w is a concept relating to a drug (Step S603). The prescription prediction reduced matrix generation module 112 determines that the medical concept w is a concept relating to a drug when the medical concept w is included in the drug list 121, for example. Further, whether or not each medical concept is a concept relating to a drug may be defined in the medical dictionary 230. In this case, the prescription prediction reduced matrix generation module 112 refers to the medical dictionary 230, and determines whether or not the selected medical concept w is a concept relating to a drug.

When it is determined that the selected medical concept w is not a concept relating to a drug (Step S603: No), the prescription prediction reduced matrix generation module 112 collects the representation vectors of the medical concept w from the representation vector set 123 (Step S604). The representation vectors to be collected in Step S604 are, for example, a representation vector represented by $\theta_w$ for the selected medical concept w.

When it is determined that the selected medical concept w is a concept relating to a drug (Step S603: Yes), the prescription prediction reduced matrix generation module 112 collects, for each target drug d, the representation vectors relating to the medical concept w in the network managed by the medical dictionary 230 centered on the target drug d from the representation vector set 123 (Step S605).

It should be noted that, for example, when the target drug d is included in the representation vector set 123, the representation vector represented by ea is included in the network centered on the target drug d. Further, a part of the representation vectors described above may be excluded from the network centered on the target drug d in accordance with an instruction from the user or the like. The representation vector to be collected in Step S605 is, for example, the representation vector represented by $\theta_w$ for the selected medical concept w.

The prescription prediction reduced matrix generation module 112 calculates a linear sum for each target drug d by multiplying each collected representation vector by a predetermined weight (an initial value other than 0) (Step S606). In the example of FIG. 4 described above, for drug A as the target drug, $\theta_{drug\ A}$ (represented as $\theta_1$ in FIG. 4), $\theta_{drug\ A\_ICER}$ (represented as $\theta_2$ in FIG. 4), and $\theta_{drug\ A\_adverse\ event}$ (represented as $\theta_3$ in FIG. 4) are collected as the phenotypic vectors, and a linear sum $\alpha_1 \theta_{drug\ A} + \alpha_2 \theta_{drug\ A\_ICER} + \alpha_3 \theta_{drug\ A\_adverse}$ event obtained by multiplying by weights $\alpha_1$, $\alpha_2$, and $\alpha_3$ is calculated as a column vector gi of the prescription prediction reduced matrix G.

After the processing of Step S604 or Step S606, the prescription prediction reduced matrix generation module 112 determines whether or not all of the selection target medical concepts have been selected (Step S607). When it is determined that there is an unselected medical concept w (Step S607: No), the prescription prediction reduced matrix generation module 112 returns to Step S602.

When it is determined that all of the selection target medical concepts have been selected (Step S607: Yes), the prescription prediction reduced matrix generation module 112 generates an initial prescription prediction reduced matrix (Step S608). Specifically, like in the example of FIG. 4 described above, the phenotypic vectors collected in Step S604 and the linear sum calculated in Step S606 are arranged as, for example, column vectors or row vectors in a predetermined order or in any order to generate the prescription prediction reduced matrix. The prescription prediction reduced matrix generation module 112 extracts a patient including the prescription of at least one target drug d from the real world data 210 (Step S609). Next, for the extracted patient, an encounter vector $x_t$ is extracted from one piece of encounter information 219, and added to the already extracted encounter vectors $x_1 \ldots, x_{t-1}$ (Step S610).

Figure 7:
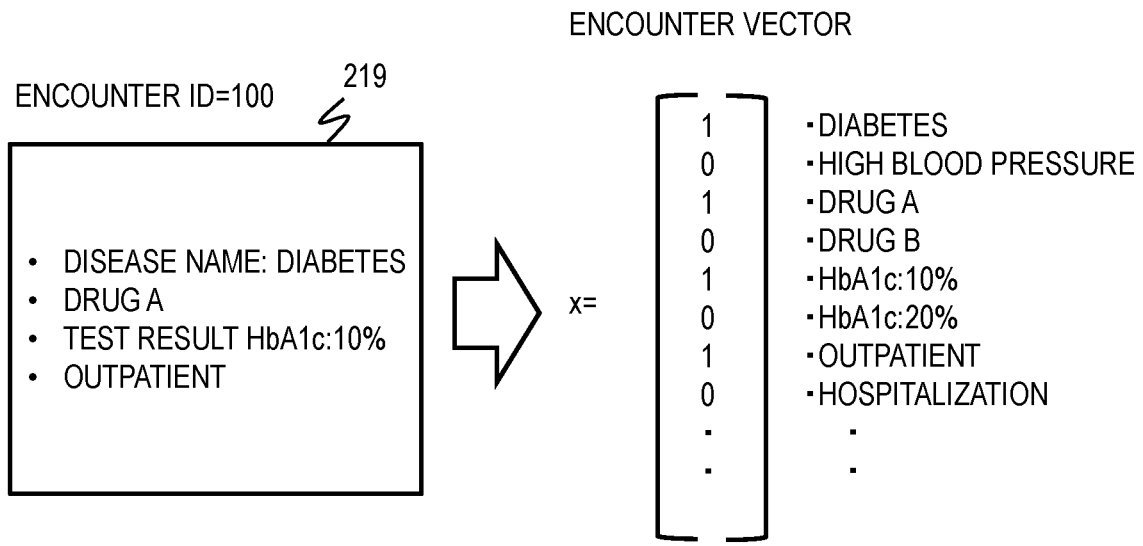
FIG. 7 is a diagram of an example of the encounter vector.

FIG. 7 is a diagram of an example of the encounter vector. Each element of the encounter vector indicates whether or not the encounter information 219 includes a value corresponding to the element (for example, 1 when the value is included, and 0 when the value is not included). The encounter vector illustrated in FIG. 7 is an encounter vector generated from the encounter information 219 having the encounter ID of "100" in FIG. 2B.

Returning to the description of FIG. 6, in the prediction using the prescription prediction model 122, the prescription prediction reduced matrix generation module 112 calculates the product of the prescription prediction reduced matrix and each of the encounter vectors $x_1, \ldots, x_t$ extracted in Step S610 (Step S611).

The prescription prediction reduced matrix generation module 112 applies the product calculated in Step S611 to the prescription prediction model 122 to acquire a predicted drug vector $y_t'$ indicating the predicted drug. The parameters of the prescription prediction model 122 are updated so as to minimize L in Expression 3 below by stochastic gradient descent, for example (Step S612). The prescription prediction reduced matrix is included in the parameters, and therefore can be updated in Step S612.

$$L(x, \ldots, x_t) = -\frac{1}{T-1}\sum_{t=1}^{T-1}\left(y_t^T \log(y_t') + (1-y_t)^T \log(1-y_t')\right) \quad \text{(Expression 3)}$$

In Expression 3, $y_t$ is a prescribed drug appearing in the encounter vector extracted in Step S610. Other variables and parameters used in Expression 3 are defined by the following Expression 4 to Expression 9.

$$g_i = \sum_{j \in A(i)} \alpha_{ij} e_j \quad \text{(Expression 4)}$$

$$\text{where } 1 = \sum_{j \in A(i)} \alpha_{ij}$$

$$\alpha_{ij} = \frac{\exp(f(e_i, e_j))}{\sum_{k \in A(i)} \exp(f(e_i, e_j))} \quad \text{(Expression 5)}$$

$$f(e_i, e_j) = u_a^T \tanh\left(W_a \begin{bmatrix} e_i \\ e_j \end{bmatrix} + b_a\right) \quad \text{(Expression 6)}$$

$$v_1, \ldots, v_t = \tanh(G[x_1, \ldots, x_t]) \quad \text{(Expression 7)}$$

$$h_1, \ldots, h_t = RNN(v_1, \ldots v_t) \quad \text{(Expression 8)}$$

$$y_t' = x_{t+1}' = \text{softmax}(Wh_t + b) \quad \text{(Expression 9)}$$

In Expression 4, A(i) represents a set of medical concepts relating to a medical concept i including a drug. In Expression 8, RNN represents a recurrent neural network. In Expression 9, softmax represents a softmax function. G is a prescription prediction reduced matrix. Further, $u_t$, $W_t$, $b_a$, W, and b are updated parameters.

In Step S612, L is minimized for each patient by stochastic gradient descent, but the parameters in the prescription prediction model 122 may be optimized by minimizing the average value of L of all patients including the prescription of the target drug d. Further, in place of stochastic gradient descent, the optimization may be performed by any optimization method for bringing the prescription prediction drug vector $y_t'$ closer to the prescribed drug vector $y_t$.

The prescription prediction reduced matrix generation module 112 then updates the weights based on the parameters updated in Step S612, recalculates the linear sum in Step S606 by using the updated weights, and updates the prescription prediction reduced matrix (Step S613). The weight indicates the degree of influence (degree of contribution) that the medical concept indicated by the corresponding representation vector has on the drug prescription indicated by the representation vector.

The prescription prediction reduced matrix generation module 112 determines whether or not the encounter vector has been extracted from all of the encounter information on the target patient (Step S614). When it is determined that there is encounter information from which the encounter vector has not yet been extracted (Step S614: No), the prescription prediction reduced matrix generation module 112 returns to Step S610. When it is determined that the encounter vector has been extracted from all of the encounter information (Step S614: Yes), the prescription prediction reduced matrix generation module 112 returns to Step S609.

The prescription prediction reduced matrix generation module 112 determines whether or not all of the patients including the prescription of at least one target drug d have been extracted (Step S615). When it is determined that there is a patient that has not yet been extracted (Step S615: No), the prescription prediction reduced matrix generation module 112 returns to Step S609. When it is determined that all of the relevant patients have been extracted (Step S615: Yes), the prescription prediction reduced matrix generation module 112 ends the prescription prediction reduced matrix generation processing.

There is described above an example in which all of the patients including the prescription of at least one target drug d are extracted, but the extraction target may be restricted to patients having a predetermined patient ID among the patients including the prescription of at least one target drug d. In addition, there is described above an example in which all of the encounter vectors are extracted from the encounter information on the patient, but the targets for extracting the encounter vector may be restricted to, for example, the encounter information on records having a date in a predetermined range among the relevant encounter information.

As a result of the prescription prediction reduced matrix being generated as described in the first embodiment, the prescription prediction model 122 including the prescription prediction reduced matrix can accurately predict a prescribed drug by considering not only the real world data 210, but also information not obtainable from the real world data 210, such as the QoL index and the ADL index.

The representation vector indicates an index having an influence on the determination of the prescribed drug, and the weight applied to the representation vector indicates the degree of influence (degree of contribution) that the medical concept indicated by the representation vector has on the prescription of the drug indicated by the representation vector. Therefore, the prescription prediction device 100 of the first embodiment can evaluate the influence that information not obtainable from the real world data 210, such as the QoL index and the ADL index, has on the determination of the prescribed drug.

Figure 8:
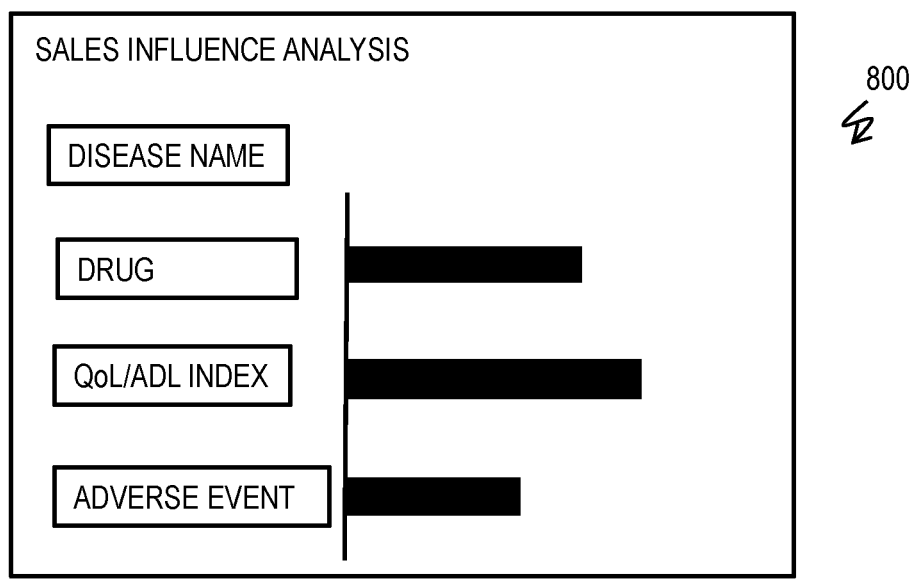
FIG. 8 is a diagram of an example of a sales influence analysis screen.

Sales influence analysis processing is now described. FIG. 8 is a diagram of an example of a sales influence analysis screen. First, the sales influence analysis processing by the sales influence analysis module 113 is described. Sales influence analysis processing is performed after the prescription prediction reduced matrix generation process ends. The sales influence analysis module 113 receives a drug designation, for example, from the user via the input interface 105 or from another device. The sales influence analysis module 113 acquires, from the representation vector set 123, the representation vectors in the network centered on the designated drug and the weights applied to those representation vectors, and outputs the acquired representation vectors and weights to the sales influence analysis screen 800.

In the example of FIG. 8, the weight of each representation vector is displayed as a graph on the sales impact analysis screen 800. This enables the user to understand how much an index not obtainable from the real world data 210 contributes to the prescription of the drug.

Figure 9:
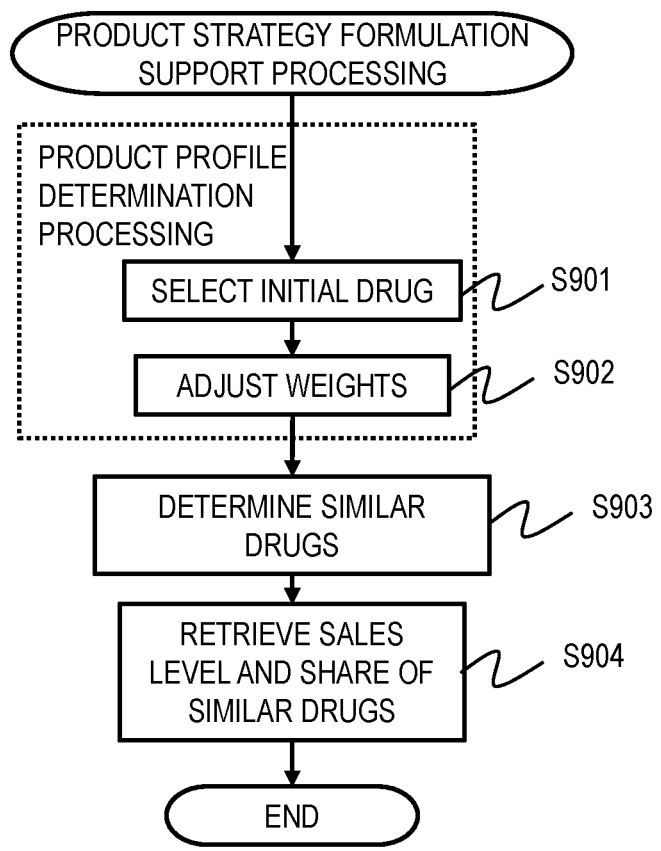
FIG. 9 is a flowchart for illustrating an example of the product strategy formulation support processing.

Product strategy formulation support processing is now described. FIG. 9 is a flowchart for illustrating an example of the product strategy formulation support processing. The product strategy formulation support processing is performed after the prescription prediction reduced matrix generation processing ends. In the product strategy formulation support processing, a drug similar to the target drug (for example, a newly developed drug) not included in a certain representation vector set 123 is retrieved.

The product strategy formulation support module 114 receives the input of the initial drug from the user via the input interface 105 or from another device, and acquires, from the representation vector set 123, the representation vectors in the network centered on the initial drug and the weight applied to those representation vectors (Step S901). In addition, for example, it is desired that a drug having an attribute close to that of the target drug be selected as the initial drug.

The product strategy formulation support module 114 adjusts the weights acquired in Step S901 (Step S902). Specifically, for example, the product strategy formulation support module 114 changes each weight to a value designated by the user. Further, for example, a threshold value of one or more weights may be set for each representation vector, and the product strategy formulation support module 114 may perform threshold value processing on each weight (for example, weights exceeding the threshold value or weights less than the threshold value are changed to be the same as the threshold value).

Further, in Step S902, the product strategy formulation support module 114 may add another representation vector not acquired in Step S901 and a weight corresponding to the another representation vector. The another representation vector and the weight corresponding to the another representation vector are designated by the user, for example. A product profile of the target drug is determined by the processing of Step S901 and Step S902.

The product strategy formulation support module 114 determines a similar drug based on the adjusted weights (Step S903). For example, the product strategy formulation support module 114 calculates the linear sum of the phenotypic vectors having the adjusted weights, calculates the vector distance between the calculated linear sum and the linear sum of the phenotypic vectors in the network of each drug, and determines that drugs having a close calculated inter-vector distance (for example, a predetermined number of drugs in order of closer distance, or drugs having distances equal to or less than a predetermined value) are similar drugs.

In addition, for example, the product strategy formulation support module 114 may calculate, for each drug, vectors in which each adjusted weight is an element and an inter-vector distance in which each weight multiplied by the representation vectors in the network of the drug is an element, and determine the drugs having a close calculated inter-vector distance to be similar drugs.

The product strategy formulation support module 114 refers to the drug sales data 124, and outputs the sales of the similar drugs, the share of the similar drugs, and the like to the output interface 108 or another device (Step S904). In addition, in Step S904, information on the similar drugs other than information on sales and shares may be displayed.

Figure 10:
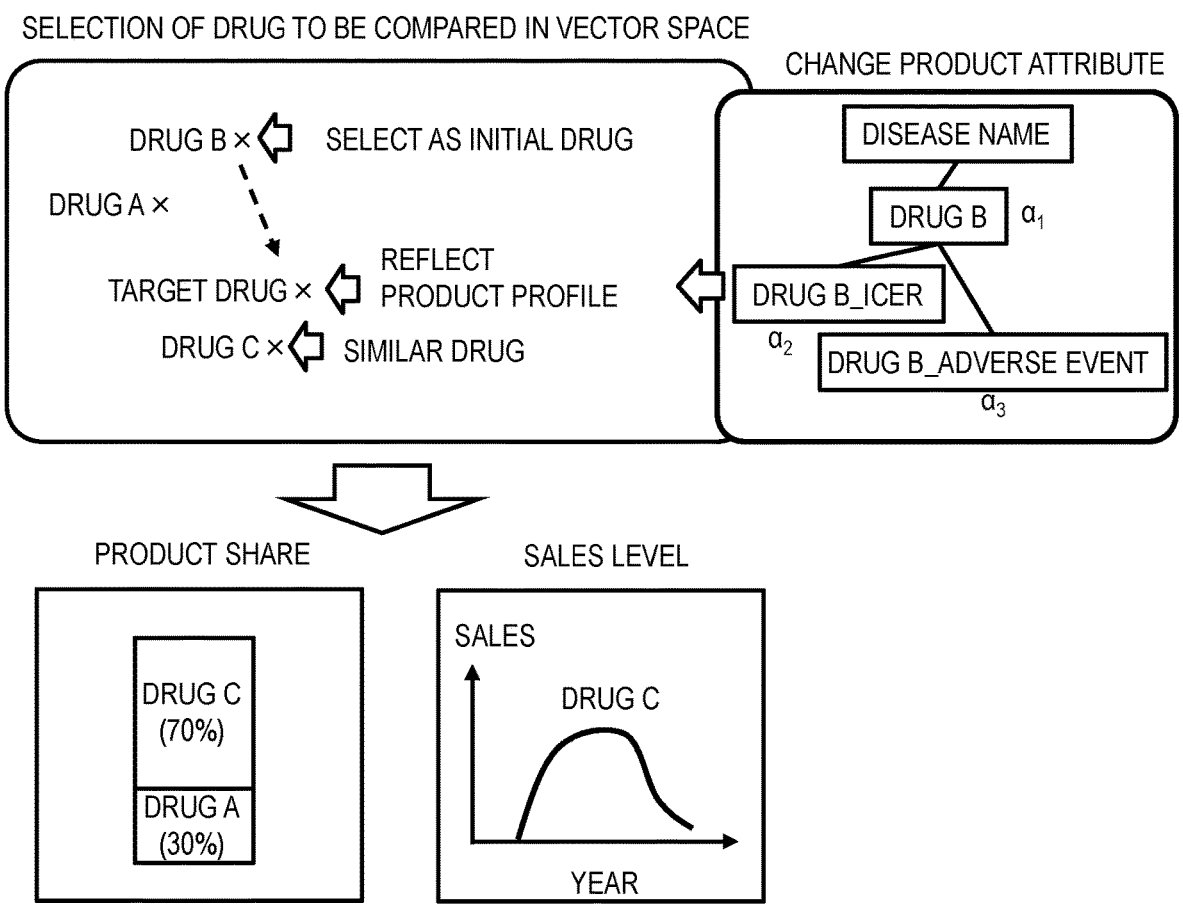
FIG. 10 is an explanatory diagram for illustrating an example of the product strategy formulation support processing.

FIG. 10 is an explanatory diagram for illustrating an example of the product strategy formulation support processing. In the example of FIG. 10, drug B is input as the initial drug for the target drug X. As illustrated in FIG. 10, as a selection of a drug to be compared in vector space, information indicating the position in the vector space of the linear sum for the target drug and each drug may be displayed.

In the example of FIG. 10, the weights $\alpha_1$, $\alpha_2$, and $\alpha_3$ for drug B, which is the initial drug, are adjusted by changing a product attribute, and it is found that the target drug is close to drug C, and drug C is selected as a similar drug. Further, the yearly sales level of drug C, which is a similar drug, and the product share of drug C in a certain year are displayed.

The product strategy formulation support processing described above enables a drug having an attribute similar to that of a drug for which representation vectors have not been generated and that is not obtainable from the real world data 210, such as the QoL and the ADL, to be determined.

This invention is not limited to the above-described embodiments but includes various modifications. The above-described embodiments are explained in details for better understanding of this invention and are not limited to those including all the configurations described above. A part of the configuration of one embodiment may be replaced with that of another embodiment; the configuration of one embodiment may be incorporated to the configuration of another embodiment. A part of the configuration of each embodiment may be added, deleted, or replaced by that of a different configuration.

The above-described configurations, functions, and processors, for all or a part of them, may be implemented by hardware: for example, by designing an integrated circuit. The above-described configurations and functions may be implemented by software, which means that a processor interprets and executes programs providing the functions. The information of programs, tables, and files to implement the functions may be stored in a storage device such as a memory, a hard disk drive, or an SSD (Solid State Drive), or a storage medium such as an IC card, or an SD card.

The drawings shows control lines and information lines as considered necessary for explanations but do not show all control lines or information lines in the products. It can be considered that almost of all components are actually interconnected.

What is claimed is:

1. A medical information processing device, comprising:
   a processor;
   a display coupled to the processor;
   an interface coupled to the processor; and
   a memory coupled to the processor,
   the memory being configured to hold:
      a medical dictionary database indicating a list of medical concepts;
      drug information database indicating a name of a drug;
      medical care information database including a medical care history; and
      documents each including a description about a medical concept other than a medical concept included in the medical care information,
   the processor being configured to:
      identify from the documents, for each combination of a medical concept other than the medical concept included in the medical care information and a drug included in the drug information, a document including the description about the medical concept and the description about the drug;
generate, for each combination, a medical concept list including the medical concept indicated by the medical dictionary included in each identified document; and
determine, based on a probability of each medical concept other than the medical concept included in the medical care information appearing in a context of the document indicated by the medical concept list, from among the medical concepts other than the medical concept included in the medical care information, a first medical concept having an influence on a prescription of the drug included in the drug information,
wherein the memory is configured to hold, when a medical care history is input, a prediction model configured to output a value indicating a predicted drug to be prescribed,
wherein the medical care history included in the medical care information includes a drug prescription history, and
wherein the processor is configured to:
determine, for each first medical concept, a degree of influence on the prescription of each drug included in the drug information;
apply a parameter indicating the degree of influence to the prediction model:
input each medical care history included in the medical care information to the prediction model having the parameter applied thereto to acquire information indicating a predicted drug;
adjust the degree of influence so that a value indicating the acquired predicted drug and a value indicating the prescribed drug indicated by the prescription history corresponding to each medical care history included in the medical care information become closer to each other; and
reflect the adjusted degree of influence in the parameter,
wherein the parameter is expressed in a matrix,
wherein the processor is configured to calculate, for each drug included in the drug information, a linear sum of products of each vector indicating the first medical concept influencing the prescription of the drug and the degree of influence corresponding to the first medical concept, and
wherein each linear sum is included as one of a row vector and a column vector of the matrix,
wherein the processor is configured to:
receive a selection via the interface of a first drug included in the drug information; and
output, to the display device, information indicating a first medical concept having an influence on the prescription of the first drug and the adjusted degree of influence corresponding to the first medical concept.

2. The medical information processing device according to claim 1,
wherein the processor is configured to:
refer to the medical dictionary to identify the medical concepts included in the medical care information;
identify, for each medical concept included in the medical care information, a medical care history including a description about the medical concept, and generate a medical concept list including the medical concepts indicated by the medical dictionary included in each identified medical care history; and
determine, based on a probability of each of the medical concepts included in the medical care information appearing in the context of the medical care history indicated by the medical concept list corresponding to the medical concept, from among the medical concepts included in the medical care information, a second medical concept having an influence on the determination of the prescribed drug, and
wherein the parameter reflects the second medical concept.

3. The medical information processing device according to claim 2,
wherein the parameter is expressed in a matrix, and
wherein the matrix has a vector indicating the second medical concept as one of a row vector and a column vector.

4. The medical information processing device according to claim 1, wherein the processor is configured to:
receive an instruction to change the output degree of influence;
change the output degree of influence based on the change instruction;
calculate a distance between the vector indicated by the changed degree of influence and the vector indicated by the adjusted degree of influence corresponding to the first medical concept having an influence on the prescription of each drug included in the drug information;
determine, based on the calculated distance, a similar drug from the drugs included in the drug information on the first drug; and
output information indicating the similar drug to the display device.

5. The medical information processing device according to claim 1,
wherein the memory is configured to hold, among the medical concepts included in the medical dictionary, numerical value relation information indicating a concept relating to a numerical value, and
wherein the processor is configured to replace, based on threshold value processing, each numerical value included in the medical concept list and indicated by the medical concept relating to a numerical value indicated by the numerical value relation information with a value having a predetermined number of stages.

6. A medical information processing method by a medical information processing device,
the medical information processing device comprising:
a processor;
a display coupled to the processor;
an interface coupled to the processor; and
a memory,
the memory being configured to hold:
a medical dictionary database indicating a list of medical concepts;
drug information database indicating a name of a drug;
medical care information database including a medical care history; and
documents each including a description about a medical concept other than a medical concept included in the medical care information,
the medical information processing method including;
identifying, by the processor, from the documents, for each combination of a medical concept other than the medical concept included in the medical care information and a drug included in the drug information, a document including the description about the medical concept and the description about the drug;

generating, by the processor, for each combination, a medical concept list including the medical concept indicated by the medical dictionary included in each identified document;

determining, by the processor, based on a probability of each medical concept other than the medical concept included in the medical care information appearing in a context of the document indicated by the medical concept list, from among the medical concepts other than the medical concept included in the medical care information, a first medical concept having an influence on a prescription of the drug included in the drug information;

holding, by the memory, when a medical care history is input, a prediction model configured to output a value indicating a predicted drug to be prescribed, wherein the medical care history included in the medical care information includes a drug prescription history, and wherein the processor is configured to perform steps comprising:

determining, for each first medical concept, a degree of influence on the prescription of each drug included in the drug information;

applying a parameter indicating the degree of influence to the prediction model;

inputting each medical care history included in the medical care information to the prediction model having the parameter applied thereto to acquire information indicating a predicted drug;

adjusting the degree of influence so that a value indicating the acquired predicted drug and a value indicating the prescribed drug indicated by the prescription history corresponding to each medical care history included in the medical care information become closer to each other; and reflecting the adjusted degree of influence in the parameter, wherein the parameter is expressed in a matrix, wherein the processor is configured to perform calculating, for each drug included in the drug information, a linear sum of products of each vector indicating the first medical concept influencing the prescription of the drug and the degree of influence corresponding to the first medical concept, and wherein each linear sum is included as one of a row vector and a column vector of the matrix, wherein the processor is configured to perform steps comprising:

receiving a selection via the interface of a first drug included in the drug information; and outputting, to the display device, information indicating a first medical concept having an influence on the prescription of the first drug and the adjusted degree of influence corresponding to the first medical concept.

7. A computer-readable non-transitory storage medium having stored thereon a program for causing a medical information processing device to execute a medical information processing, the medical information processing device comprising:
a processor;
a display coupled to the processor;
an interface coupled to the processor; and
a memory coupled to the processor, the memory being configured to hold:
a medical dictionary database indicating a list of medical concepts;
drug information database indicating a name of a drug;
medical care information database including a medical care history; and
documents each including a description about a medical concept other than a medical concept included in the medical care information, the program causing the medical information processing device to execute:

identifying from the documents, for each combination of a medical concept other than the medical concept included in the medical care information and a drug included in the drug information, a document including the description about the medical concept and the description about the drug;

generating, for each combination, a medical concept list including the medical concept indicated by the medical dictionary included in each identified document; and determining, based on a probability of each medical concept other than the medical concept included in the medical care information appearing in a context of the document indicated by the medical concept list, from among the medical concepts other than the medical concept included in the medical care information, a first medical concept having an influence on a prescription of the drug included in the drug information, wherein the memory is configured to hold, when a medical care history is input, a prediction model configured to output a value indicating a predicted drug to be prescribed, wherein the medical care history included in the medical care information includes a drug prescription history, and wherein the processor is configured to:

determine, for each first medical concept, a degree of influence on the prescription of each drug included in the drug information;

apply a parameter indicating the degree of influence to the prediction model;

input each medical care history included in the medical care information to the prediction model having the parameter applied thereto to acquire information indicating a predicted drug;

adjust the degree of influence so that a value indicating the acquired predicted drug and a value indicating the prescribed drug indicated by the prescription history corresponding to each medical care history included in the medical care information become closer to each other; and reflect the adjusted degree of influence in the parameter, wherein the parameter is expressed in a matrix, wherein the processor is configured to calculate, for each drug included in the drug information, a linear sum of products of each vector indicating the first medical concept influencing the prescription of the drug and the degree of influence corresponding to the first medical concept, and wherein each linear sum is included as one of a row vector and a column vector of the matrix, wherein the processor is configured to:

receive a selection via the interface of a first drug included in the drug information; and output, to the display device, information indicating a first medical concept having an influence on the prescription of the first drug and the adjusted degree of influence corresponding to the first medical concept.

* * * * *